United States Patent
Sauerland et al.

(10) Patent No.: US 7,066,919 B1
(45) Date of Patent: Jun. 27, 2006

(54) ALARM FOR A FLUID-DISPENSING/RECEIVING RECEPTACLE

(76) Inventors: Keith A. Sauerland, 236 Cross Creek La., Lindenhurst, IL (US) 60046;
Arlene K. Sauerland, 236 Cross Creek La., Lindenhurst, IL (US) 60046

( * ) Notice: Subject to any disclaimer, the term of this patent is extended or adjusted under 35 U.S.C. 154(b) by 0 days.

(21) Appl. No.: 11/125,361

(22) Filed: May 9, 2005

(51) Int. Cl.
*A61F 5/44* (2006.01)

(52) U.S. Cl. .................. 604/327; 604/317; 604/332

(58) Field of Classification Search ........ 340/603–604, 340/612, 623–624, 332–344, 686.1, 687, 340/686.4, 573.1, 618; 304/612; 335/125; 604/332–344
See application file for complete search history.

(56) References Cited

U.S. PATENT DOCUMENTS

| | | | | |
|---|---|---|---|---|
| 4,224,610 A | * | 9/1980 | Quinby | 340/614 |
| 4,378,014 A | * | 3/1983 | Elkow | 604/48 |
| 4,573,984 A | * | 3/1986 | Benzies | 604/339 |
| 5,121,107 A | * | 6/1992 | Newell | 340/618 |
| 5,409,014 A | | 4/1995 | Napoli et al. | |
| 5,989,235 A | | 11/1999 | Quacquarella et al. | |
| 6,135,986 A | | 10/2000 | Leisner et al. | |
| 6,171,288 B1 | | 1/2001 | Wiltshire | |
| 6,218,949 B1 | * | 4/2001 | Issachar | 340/624 |
| 6,296,627 B1 | | 10/2001 | Edwards | |
| 6,695,825 B1 | | 2/2004 | Castles | |

FOREIGN PATENT DOCUMENTS

GB     2063071 A  *  6/1981

\* cited by examiner

*Primary Examiner*—Tatyana Zalukaeva
*Assistant Examiner*—Keshia Gibson
(74) *Attorney, Agent, or Firm*—Meroni & Meroni, P.C.; Charles F. Meroni, Jr.; Christopher J. Scott (57) ABSTRACT

A fluid receptacle alarm assembly and/or kit comprising a fluid receptacle, an alarm module and at least one magnetic field source. The alarm module comprises an alarm, a magnetically-actuated switch, and a power source. The alarm module is attachable to a first surface of the fluid receptacle and the magnetic field source is attachable to a second surface of the fluid receptacle. A fluid quantity is receivable intermediate the first and second receptacle surfaces for adjusting the distance intermediate the first and second receptacle surfaces. The magnetic field source actuates the switch when a select alarm activation distance is adjustably met. The actuated switch electrically communicates the power source with the alarm. The energized alarm alerts a user to the fluid quantity in the fluid receptacle.

10 Claims, 9 Drawing Sheets

ALARM FOR A FLUID-DISPENSING/RECEIVING RECEPTACLE

BACKGROUND OF THE INVENTION

1. Field of the Invention

The present invention generally relates to an alarm system for use in conjunction with fluid containment bags. More particularly, the present invention relates to an alarm system for use in conjunction with fluid-dispensing/receiving receptacles, such as urine collection bags, ostomy bags, and/or intravenous fluid bags for alerting the user to a dynamically developing fluid quantity in the fluid receptacle.

2. Description of the Prior Art

In the course of everyday hospital work, hospital personnel often encounter many patients that, due to various forms of cancer, no longer have a urinary bladder and therefore must make use of a urine-collection bag or ostomy bag. Before performing any of a number of tests on the patient, many patients often inquire of the hospital personnel whether their urine-collection bag or ostomy bag will interfere with the test. In most instances, the answer to this question is "No", but it is often beneficial to have the patient empty the bag before the test. After the bag is emptied, the patient occasionally remarks that he or she has gotten used to "the extra weight from the bag" and then forgets to empty it before the bag becomes too full. Emptying an otherwise overladen urine-collection bag or ostomy bag can be quite a task and is oftentimes messy and embarrassing, particularly when the process must occur away from the privacy of the user's home. The possibility of a urine-collection bag or ostomy bag having a leak or overflowing when full at the time of detachment or emptying is thus a significant possibility. This problem has resulted in great concern and embarrassment for those persons required to make use of such a device.

Thus, it has come to the inventors' attention, when discussing these and similar other difficulties with patients utilizing such bags, that there is a need for some way to attend to this problem, the problem being that quite often the users of such bags have found that their bags become full and they were unaware that the condition was at hand. A number of devices have been developed in an effort to improve the effectiveness of fluid containment bags, several of which are described in brief detail hereinafter.

U.S. Pat. No. 6,695,825 ('825 patent), which issued to Castles, discloses a Portable Ostomy Management Device. The '825 patent teaches a portable, self-contained, powered unit designed to wash and clean the stoma, and interior of drainable ostomy pouches. These pouches are designed to accept the human body waste via the stoma, located on the body of an ostomy patient. This portable system allows an ostomate to position the pouch so it drains into a toilet bowl, permitting the person to wash the pouch interior without removing it from the body or from the barrier section. This portable device allows the ostomate to completely service the ostomy in just a few minutes. The invention includes a carrying case (briefcase, travel bag, soft case, or other containing device), water reservoir, power unit, pump, hoses, control valve, and various other components necessary in controlling power, water pressure and other attributes of this device.

U.S. Pat. No. 6,171,288 ('288 patent), which issued to Wiltshire, discloses an Ostomy Bag. The '288 patent teaches a vented ostomy bag with a gas filter is described, the bag having a top and a bottom and comprising first and second outer walls sealed around their edges, the first outer wall incorporating a stoma-receiving opening. The bag further comprises first and second intermediate walls also sealed with the first and second outer walls around their edges to provide between the first outer and first intermediate walls a first chamber, between the first and second intermediate walls a second chamber and between the second intermediate and second outer walls a third chamber. A first gas vent is provided in the first intermediate wall between the first and second chambers for the passage of gas there between, and a second gas vent is provided in the second intermediate wall between the second and third chambers for the passage of gas there between. A gas passage is provided from the third chamber out of the bag which passes through the gas filter.

U.S. Pat. No. 6,135,986 ('986 patent), which issued to Leisner, et al., discloses an Ostomy Appliance. The '986 patent teaches an ostomy appliance comprising a front wall and a rear wall of flexible material, the rear wall having an opening into the bag by which waste material can enter the bag and one of the walls has one or more vents through which gas may escape from the bag and having a filter covering said vent, said filter comprising an elongated, substantially flat filter body of a porous filter material interposed between gas and liquid impervious walls which are sealed to the body along its longitudinal side edges; gas inlet and outlet openings being provided in communication with the filter material adjacent to its respective longitudinal end regions, wherein both of the gas and liquid impervious walls are sealed to the upper end lower surfaces of the filter body, the arrangement being so that in use gas flows longitudinally through the filter from the inlet opening to the outlet opening, such gas flow being by a hydrophobic sheet, wherein the inlet opening is covered with a microporous oleophobic membrane and wherein a foam material is placed between the front wall and the rear wall and covering the inlet opening of the vent shows improved resistance against wetting and blocking of the filter.

U.S. Pat. No. 5,989,235 ('235 patent), which issued to Quacquarelle, et al., discloses an Ostomy Bag. The '235 patent teaches a drainage bag (colostomy, ileostomy or urostomy bag) comprising a bag of thermoplastic material having means to define an opening for receiving waste material from a stoma and means to secure the bag in place with the opening connected to the stoma, characterized in that at least the surface of the bag in contact with the skin of the wearer is flocked. Also described is an ostomy appliance comprising a re-usable outer bag and a disposable inner bag, means for securing the two bags together and to the stoma, means for inserting and removing the inner bag from the outer one, and means for closing, the outer bag once the inner one is in place, characterized in that at least the surface of the outer bag in contact with the skin of the wearer is flocked.

U.S. Pat. No. 6,296,627 ('627 patent), which issued to Edwards, discloses a Urine Collection System. The '627 patent teaches a urine collection system for use by a person using a float tube, the system comprising a flexible pouch housing a urine collection reservoir in fluid communication with the person. The pouch defines first and second openings, one for receiving a tube connected to the urine collection reservoir that is coupled to the user with a condom catheter and a second for receiving a drainage valve for conveniently emptying urine from the reservoir. A unidirectional valve is associated with the tube for preventing urine from exiting the reservoir while allowing urine to freely enter the reservoir. The pouch is preferably placed outside the float tube at or above the water level so that water pressure does not affect the operation of the urine collection system.

U.S. Pat. No. 5,409,014 ('014 patent), which issued to Napoli, et al., discloses a Fluid Meter. The '014 patent teaches a fluid meter for measuring fluids such as urine, which meter includes a connector for connecting and disconnecting a urine collection bag thereto. The fluid meter may also include a connector for connecting and disconnecting the meter from a catheter drain tube. In the preferred embodiment, the urine meter includes a container having an inlet and outlet. A male connector is operatively attached to the container outlet for connecting and disconnecting the container from a female connector attached to the urine collection bag. Similarly, a female connector is operatively attached to the container inlet for connecting and disconnecting the container from a male connector attached to the drain tube. As an additional feature, the female connector of the urine collection bag may be connected directly to the male connector of the drain tube with the urine meter disconnected therefrom.

It will thus be seen from an inspection of the prior art that there appears to be no devices that convey a warning to the wearer of an ostomy bag, that the ostomy bag has become filled to a critical level of containment that will result in a spill or leakage. Further, it will be noted that when the use of an intravenous electronic/mechanical measuring pump is not an option nor is available, the prior art does not teach an apparatus or method for alerting nurses or caregivers that an intravenous fluid bag is nearing empty while in use by a patient. The condition of having a lack of fluid flow to the patient can create a variety of complications. Thus, it will be seen that the prior art does not provide a device for warning of the approaching empty condition of an intravenous fluid bag when not used in conjunction with an electronic/mechanical measuring pump.

Thus, the prior art perceives a need for an alarm that quietly but firmly warns an ostomy or urine collection receptacle of an impending leak and contamination accident because of its volume state or fullness.

SUMMARY OF THE INVENTION

To accomplish the goal of providing an alarm to warn an ostomy bag wearer or urine collection bag wearer of the possible rupture or leak due to the overfilling of a containment bag for urine or feces, the claimed invention provides a quiet vibrating alarm with a self actuation feature when used in conjunction with a specialized bag.

A further objective of the claimed invention is thus to provide a simple device that can warn a urine or ostomy bag wearer of the fullness of the bag in a discrete or inconspicuous manner. A further objective is to provide an alarm that does not necessitate a manually operated power function switch. The use of such an automatic switching method prevents the unwanted discharge of the operating battery by accidental activation when not in the pocket provided on the outside of the bag.

To accomplish the additional goal of providing an audible warning device to alert caregivers within hearing range of the approach of a low level of fluid in an intravenous fluid bag that is providing fluid to a patient. This use of the alarm is recommended when there is no electronic-mechanical measuring pump that would otherwise provide the warning.

Still further, an objective of the claimed invention is to provide an alarm device that is totally sealed at the time of production. This allows such a device to be wiped clean of any contamination without damaging the electronics inside.

To achieve these and other readily apparent objectives, the present invention provides a vibrating or audible alarm for cooperative association with a urine collection bag or similar other ostomy bag as well as intravenous fluid bags. The alarm generally comprises a vibrating device or loud audible device, a single-throw double pole slide switch to select the warning method, two dry reed switches, and a Lithium disc battery that places the device into an operating mode by magnets that actuate the dry reed switches.

The overall minimal size and shape of the alarm housing, when used in cooperative association with a urine-collection bag or similar other ostomy bag, allows the user to wear it in a small outside pocket of the ostomy bag with little or no awareness of the bulk by the wearer. The size of the housing is generally on the order of 2 inches by 2.5 inches by 0.375 inches.

Thus, the present invention essentially comprises a combination fluid receptacle and alarm assembly, the alarm assembly for alerting a user of the fluid receptacle to a dynamic fluid quantity formed therein. The fluid receptacle comprises a flexible fluid-impermeable casing, fluid passage means, and first and second receptacle surfaces. The first and second receptacle surfaces are adjustably distant from one another. The adjustably distant first and second receptacle surfaces have a select alarm activation distance therebetween. The alarm assembly comprises an alarm module and at least one magnetic field source. The alarm module comprises select user alert means, magnetically-actuated switch means, and power source means. The alarm module is attached to the first receptacle surface and the magnetic field source is attached to the second receptacle surface. The fluid passage means enable dynamic fluid quantity development intermediate the first and second receptacle surfaces. The dynamic fluid quantity inherently has a dynamic volume, the dynamic volume for adjusting the linear distance intermediate first and second receptacle surfaces. The magnetic field source actuates the switch means when the select alarm activation distance is adjustably met. The actuated switch means electrically communicate the power source means with the select user alert means thus energizing the select user alert means. The energized select user alert means alert a user to the dynamic fluid quantity in the fluid receptacle.

BRIEF DESCRIPTION OF THE DRAWINGS

Other features of our invention will become more evident from a consideration of the following brief description of our patent drawings, as follows:

FIG. No. 1 is a fragmentary front plan view of the preferred combination alarm assembly and fluid-dispensing/receiving receptacle attached to a user's leg.

FIG. No. 2 is a fragmentary front plan view of the preferred fluid-dispensing/receiving receptacle attached to a user's leg.

FIG. No. 3 is a fragmentary side plan view of the preferred fluid-dispensing/receiving receptacle attached to a user's leg showing a first magnetic field source.

FIG. No. 4 is a fragmentary side plan view of the preferred combination alarm assembly and fluid-dispensing/receiving receptacle attached to a user's leg showing a first fluid quantity level formed in the fluid-dispensing/receiving receptacle.

FIG. No. 5 is a fragmentary side plan view of the preferred combination alarm assembly and fluid-dispensing/receiving receptacle attached to a user's leg showing a second fluid quantity level formed in the fluid-dispensing/ receiving receptacle, the second fluid quantity level activating the alarm assembly.

FIG. No. 6(a) is a front plan view of the fluid-dispensing/ receiving receptacle showing a pocket cooperatively associated with a first receptacle surface.

FIG. No. 6(b) is a back plan view of the fluid-dispensing/ receiving receptacle showing a second magnetic field source cooperatively associated with a second receptacle surface.

FIG. No. 7 is a front plan view of the pocket with parts broken away to show a first magnetic field source cooperatively associated with the first receptacle surface.

FIG. No. 8 is a side plan view of the fluid-dispensing/ receiving receptacle showing the pocket, and first and second magnetic field sources.

FIG. No. 9 is an enlarged front plan view of the pocket.

FIG. No. 10 is an enlarged front plan view of the pocket with parts broken away to show the first magnetic field source cooperatively associated with the first receptacle surface.

FIG. No. 11 is a front plan view of an alternative fluid-dispensing/receiving receptacle showing indicia for locating an alarm module.

FIG. No. 12 is a back plan view of the alternative fluid-dispensing/receiving receptacle showing indicia for locating the second magnetic field source.

FIG. No. 13(a) is a front plan view of an alarm module housing showing an alert means selection switch in a first position.

FIG. No. 13(b) is a front plan view of the alarm module housing showing the alert means selection switch in a second position.

FIG. No. 14 is a top plan view of the alarm module showing various components.

FIG. No. 15 is a side edge view of the alarm module shown in FIG. No. 14.

FIG. No. 16 is a circuit diagram depicting various components of the alarm module.

DETAILED DESCRIPTION OF THE PREFERRED EMBODIMENT

Referring now to the drawings, the preferred embodiment of the present invention concerns an alarm assembly 10 as generally illustrated and referenced in FIG. Nos. 1, 4, 5, 13(a), and 13(b). Alarm assembly 10 is designed for use in combination with a fluid-receiving/dispensing receptacle 90 as further illustrated and referenced in FIG. Nos. 1–6(b), 8, 11, and 12. Alarm assembly 10 functions to alert a user of fluid-receiving/dispensing receptacle 90 to a dynamically developing fluid quantity 100 in fluid-receiving receptacle 90 as comparatively depicted in FIG. Nos. 4 and 5 at reference numeral 100. In other words, it is contemplated that fluid-receiving receptacle 90 is designed to either receive fluid incrementally or to dispense fluid decrementally and thus an initial fluid quantity may either be incremented by certain amounts at a certain incremental rate or decremented by certain amounts at a certain decremental rate.

In this regard, it is contemplated that a fluid-receiving receptacle such as a urine collection bag or similar other fluid-receiving bag, such as an ostomy bag, may receive an incremental fluid quantity as typically formed through incoming fluid droplets 101 as generally depicted and referenced in FIG. Nos. 4 and 5. Further, it is contemplated that a fluid-dispensing receptacle, such as an intravenous bag, may dispense a decremental fluid quantity as formed through outgoing fluid droplets as generally depicted in FIG. Nos. 11 and 12. It is contemplated that the most common usage of the present invention will be for outfitting urine collection bags. Thus, it is contemplated that in the preferred embodiment, fluid-dispensing/receiving receptacle 90 is an inconspicuously worn urine-collection bag (or ostomy bag) as generally depicted in FIG. Nos. 1–8. An alternative usage may be for outfitting intravenous bags, as generally depicted in FIG. Nos. 11 and 12.

Figure 1:
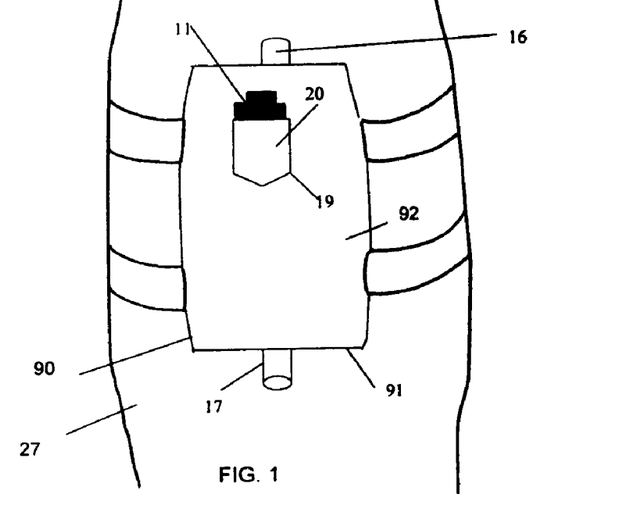
Figure 2:
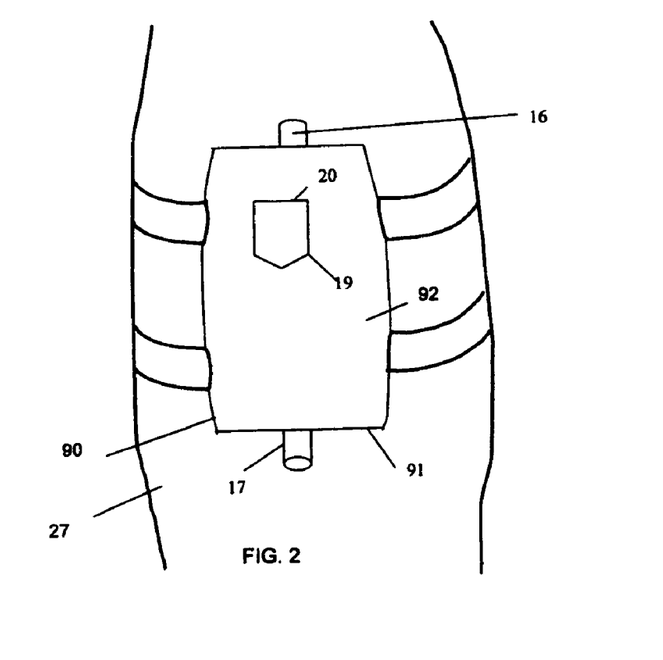
Figure 3:
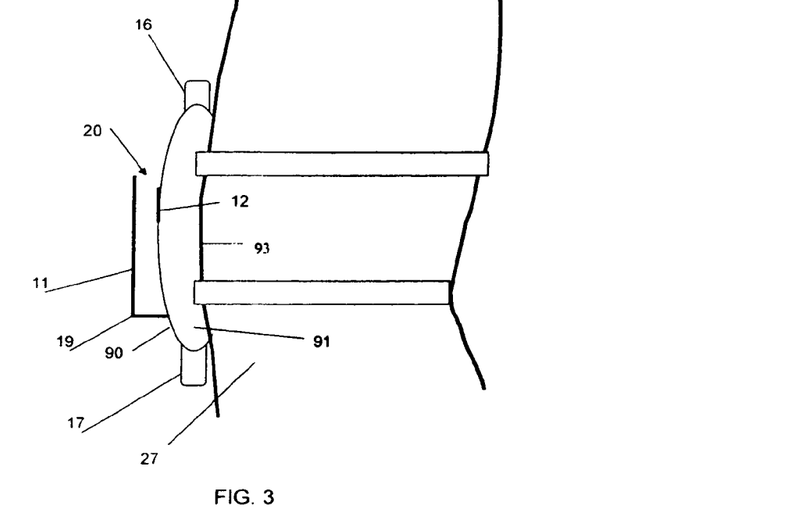
Figure 4:
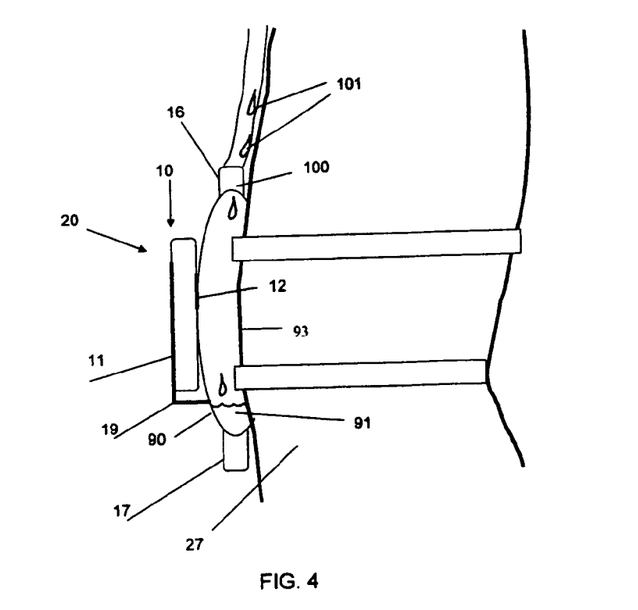
Figure 5:
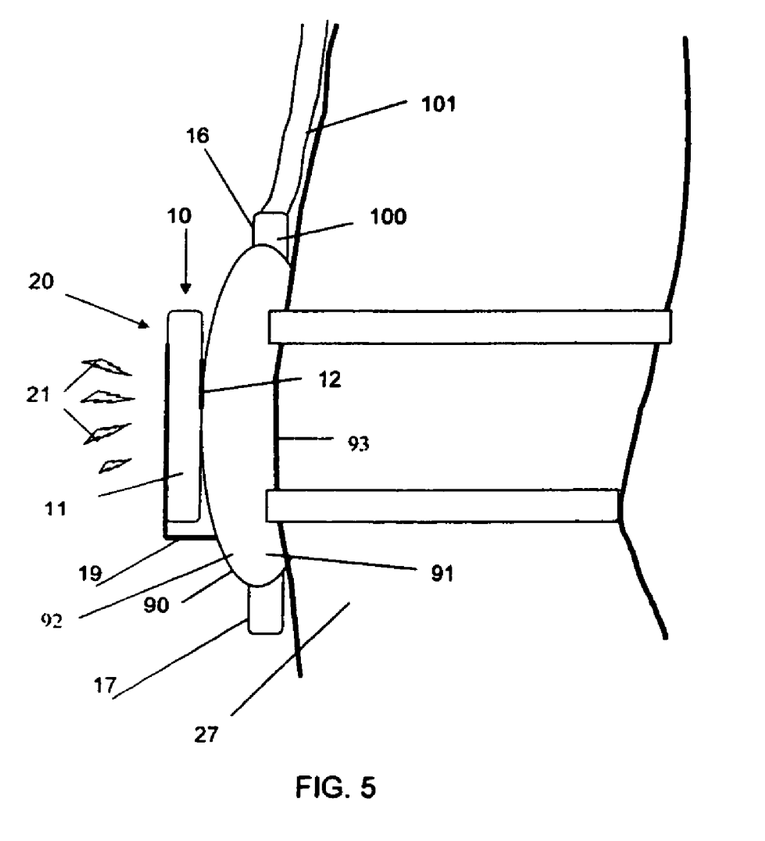
Figures 6A, 6B, 7, 8:
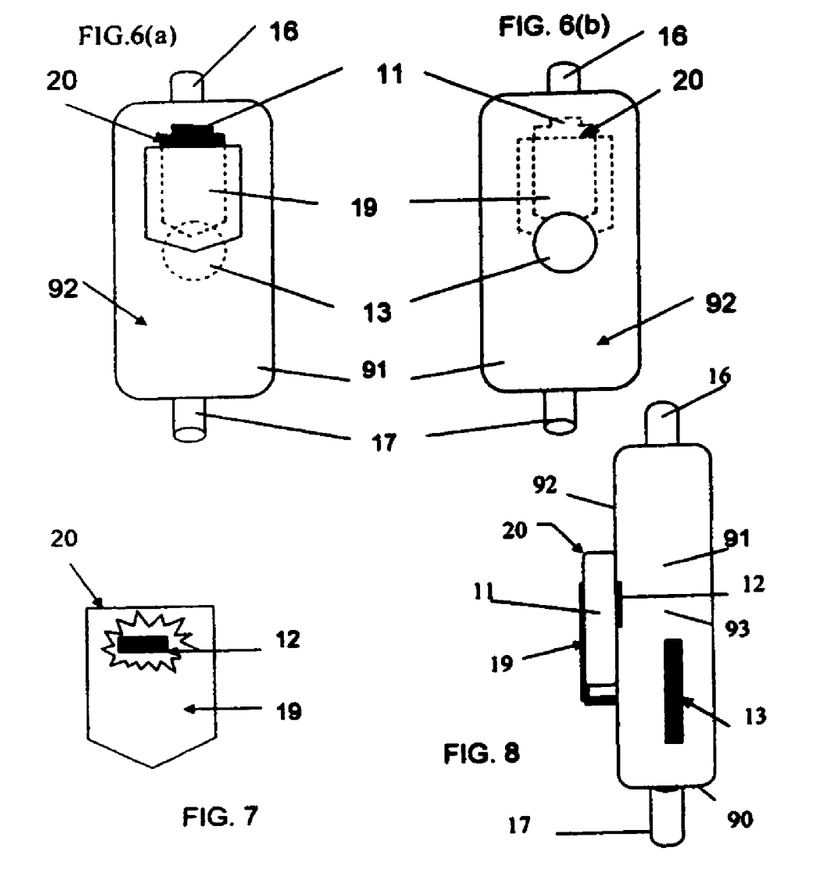
Figure 9:
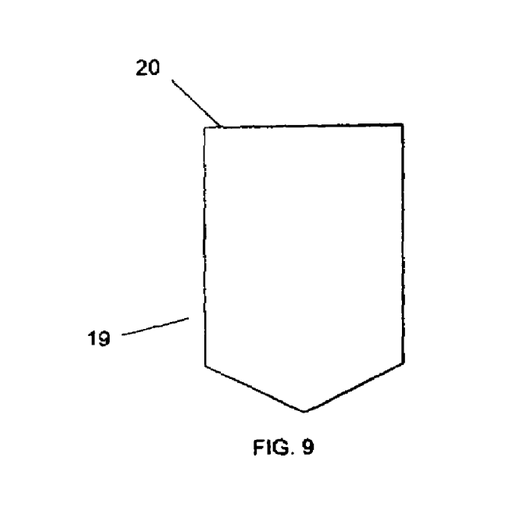
Figure 10:
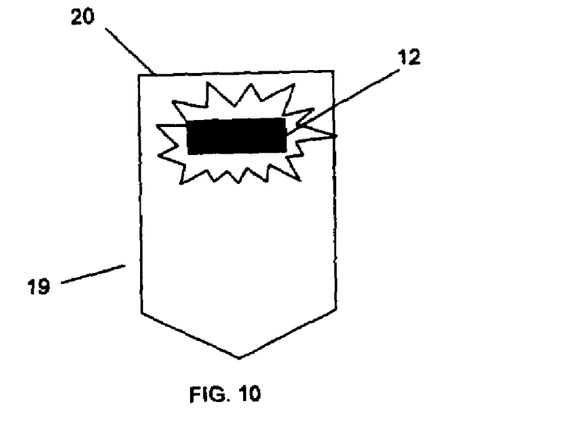

From a comparative inspection of FIG. Nos. 4 and 5 it will be seen that as dynamically developing fluid quantity 100 develops, fluid-receiving/dispensing receptacle 90 becomes fuller (i.e. FIG. No. 4 depicts fluid-receiving/dispensing receptacle 90 in a near empty state and FIG. No. 5 depicts fluid-receiving/dispensing receptacle 90 in a full state). Notably, the incrementing fluid quantity has an incremental volume, each incoming fluid droplet 101 having a certain liquid volume, however, infinitesimal. The incremental volume essentially expands the interior of fluid-receiving/ dispensing receptacle 90 as is generally shown in FIG. No. 5. Given a fluid-receiving receptacle, it is this expansion that operates to set off alarm assembly 10 and thereby alert the user of the alarm assembly 10 that it is time to otherwise adjust the incremental volume forming within fluid-receiving/dispensing receptacle 90 (e.g. by emptying the urine collection bag).

Notably, fluid-receiving/dispensing receptacle 90 preferably comprises a flexible or adjustable fluid-impermeable casing as generally referenced at 91 in FIG. Nos. 1–6(b), 8, 11, and 12; fluid passage means, a first receptacle surface 92 as illustrated and referenced in FIG. Nos. 1–6(a), 8, and 11; and a second receptacle surface 93 as illustrated and referenced in FIG. Nos. 3, 4, 5, 6(b), 8, and 12. Being constructed from a flexible or adjustable casing 91, the first and second receptacles surfaces 92 and 93 of fluid-receiving/dispensing receptacle 90 are adjustably distant from one another as may be seen from a comparative inspection of FIG. Nos. 4 and 5. The adjustably distant first and second receptacle surfaces 92 and 93 inherently have a select alarm activation distance therebetween. In other words, as dynamically developing fluid quantity 100 develops, a certain fluid volume operates to either expand or contract casing 91 and thus first receptacle surface 92 translates or becomes otherwise displaced from second receptacle surface 93. Depending on the further key components, the select alarm activation distance between first and second receptacles surfaces 92 and 93 operates to actuate certain alert means for notifying the user of alarm assembly 10 to dynamically developing fluid quantity 100 forming in fluid-receiving/dispensing receptacle 90.

Alarm assembly 10 preferably comprises an alarm module 11 as illustrated and referenced in FIG. Nos. 1, 4, 5, 6(a), 6(b), 8, 13(a), 13(b), 14, and 15; a first magnetic field source 12 as illustrated and referenced in FIG. Nos. 3, 4, 5, 7, 8, 10, 13(a), and 13(b); and a second magnetic field source 13 as illustrated and referenced in FIG. Nos. 6(a), 6(b), 8, 13(a), and 13(b). Alarm module 11 preferably comprises select user alert means, a magnetically-actuated, normally closed first switch 15 as illustrated and referenced in FIG. Nos. 14–16; a magnetically-actuated, normally open second switch 14 as illustrated and referenced in FIG. Nos. 14–16; and power source means. The power source means may preferably be defined by a (3 volt) lithium battery 24 as illustrated and referenced in FIG. Nos. 14–16; first and second magnetically-actuated switches 14 and 15 are defined by first and second dry reed switches, and the first and second magnetic field sources are defined by first and second neodium magnets. Lithium battery 24, the dry reed switches, and the neodium magnets are each preferably minimally sized and shaped so as to maintain the inconspicuousness of the inconspicuously worn urine collection bag. The size of the alarm module housing (as generally illustrated in FIG. Nos. 13(*a*) and 13(*b*) is on the order of 2 inches by 2.5 inches by 0.375 inches.

Alarm module 11 and first magnetic field source 12 are preferably attached to first receptacle surface 92 as generally depicted in FIG. Nos. 4 and 5. Second magnetic field source 13 is preferably attached to second receptacle surface 93 as generally depicted in FIG. Nos. 6(*b*), and 8. First and second magnetic field sources 12 and 13 operate to actuate first and second switches 15 and 14, respectively. In the fluid-receiving embodiment of the present invention, the fluid passage means function to enable a fluid quantity to increment (i.e. dynamically developing fluid quantity 100) intermediate first and second receptacle surfaces 92 and 93. The incrementing fluid quantity inherently has an incremental volume, which increases the distance intermediate first and second receptacle surfaces 92 and 93 as generally depicted in FIG. Nos. 4 and 5. Second magnetic field source 13 deactuates second switch 14 when the select alarm activation distance is adjustably met. The deactuated second switch 15 electrically communicates the power source means with the select user alert means thus energizing the select user means. The energized select user alert means alert a user of alarm assembly 10 to the incremental fluid quantity in the fluid-receiving receptacle (i.e. fluid-dispensing/receiving receptacle 90).

First receptacle surface 92 preferably comprises a pocket 19 as illustrated and referenced in FIG. Nos. 1–10. From an inspection of the noted figures it will be seen that pocket 19 comprises an open end 20 for removably attaching alarm module 10 to first receptacle surface 92. From a general inspection of FIG. Nos. 1, 4, and 5, and from a comparative inspection of FIG. Nos. 9 and 10 versus FIG. Nos. 13(*a*) and 13(*b*), it will be seen that pocket 19 is sized and shaped to receive alarm module 11 such that first magnetic field source 12 is positioned immediately adjacent first switch 14 for actuating (closing) the normally open switch and further such that second magnetic field source 13 is positioned laterally adjacent second switch 15 (it being again noted that second magnetic field source 13 is attached to second receptacle surface 93).

Alarm module 11 may preferably comprise audible alert means (such as a periodic or constant tone or periodic or constant buzzer), visual alert means (such as a flashing or constant light emitting diode or flashing or constant light), and tactile alert means (such as a vibrating mechanism), all of which have been generically depicted at reference numeral 21 in FIG. No. 5. From an inspection of FIG. Nos. 14–16 it will be seen that the present invention contemplates a low voltage, low current miniature vibrating motor 22 (for inconspicuous use as a urine/ostomy bag alarm) and a piezo alarm/buzzer 23 (for use in intravenous bag scenarios). The select user alert means may thus be selected from the group consisting of the audible alert means, the visual alert means, and the tactile alert means. In this regard, it is contemplated that alarm assembly 10 may comprise various means for alerting the user to the dynamically developing fluid quantity 100. Some users may wish to utilize the relatively inconspicuous tactile alert means so that passersby may not become otherwise alerted to the dynamically developing fluid quantity 100. Others may prefer visual or audible alert means and thus it is contemplated that alarm assembly 10 may provide the user with various alert means from which the user may select the most preferable form.

It will thus be seen from an inspection of FIG. Nos. 14–16 that alarm assembly 10 preferably further comprises a selector slide switch 18 as illustrated and referenced in FIG. Nos. 13(*a*), 13(*b*), 14, 15, and 16. In the preferred, fluid-receiving embodiment, the fluid passage means may comprise a fluid inlet 16 as illustrated and referenced in FIG. Nos. 1–6(*b*), and 8; and a fluid outlet 17 as further illustrated and referenced in FIG. Nos. 1–6(*b*), and 8. In the preferred embodiment, fluid inlet 16 functions to increment the incremental fluid quantity at an incremental rate and fluid outlet 17 functions to selectively decrement the incremental fluid quantity at a decremental rate (e.g. empty the urine collection bag). Notably, when the user is alerted to the dynamically developing fluid quantity 100, he or she may selectively engage the fluid outlet and thus it is contemplated that the decremental rate be greater than the incremental rate, thus selectively forming a decremental fluid quantity intermediate the first and second receptacle surfaces 92 and 93. The decremental fluid quantity essentially decreases the linear distance intermediate the first and second receptacle surfaces 92 and 93, bringing second magnetic field source 13 into closer contact with second switch 14, thus closing the normally open second switch 14, thereby resetting the select user alert means.

Figure 11:
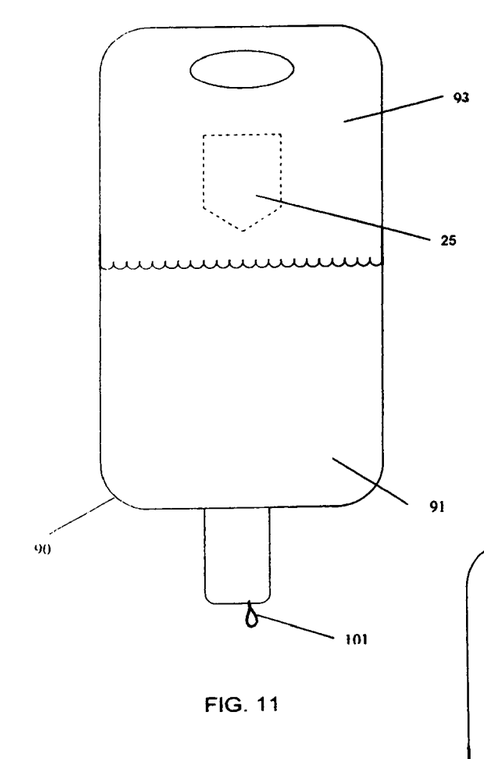
Figure 12:
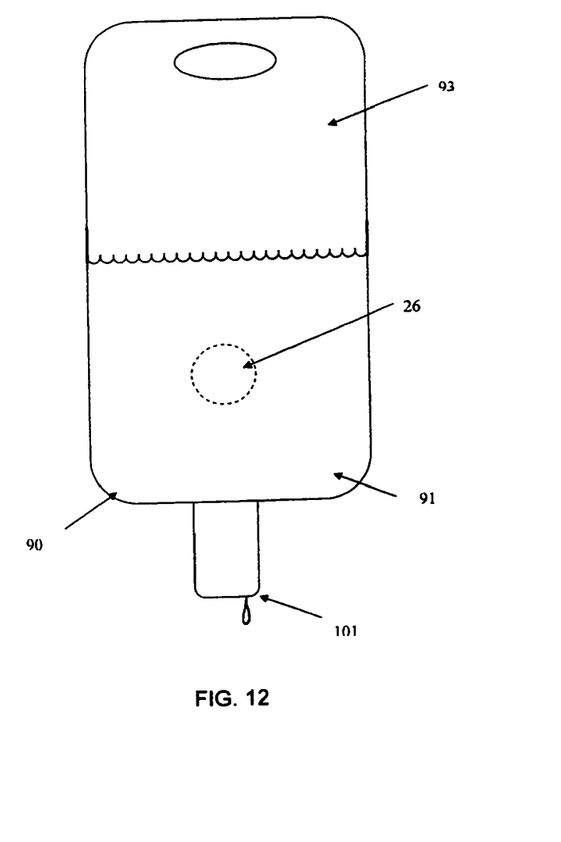
Figure 13:
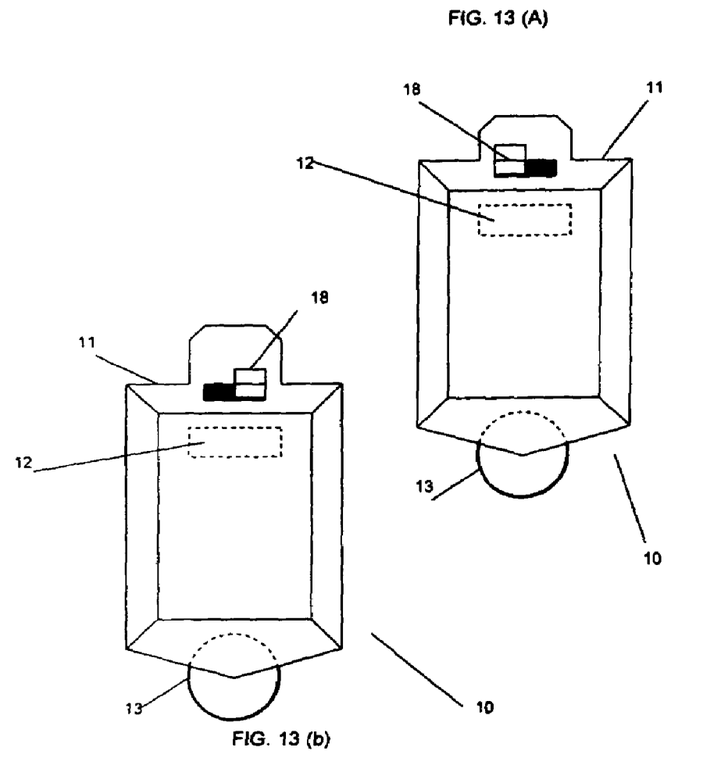
Figure 14:
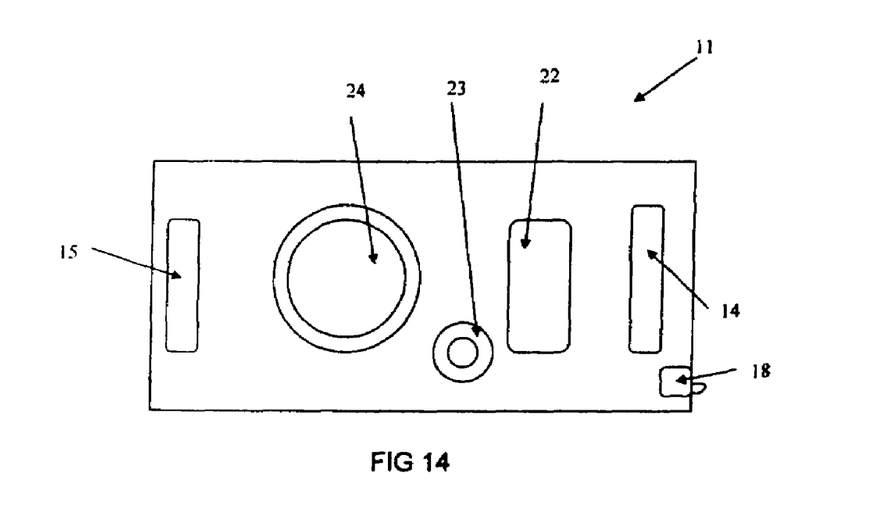
Figure 15:
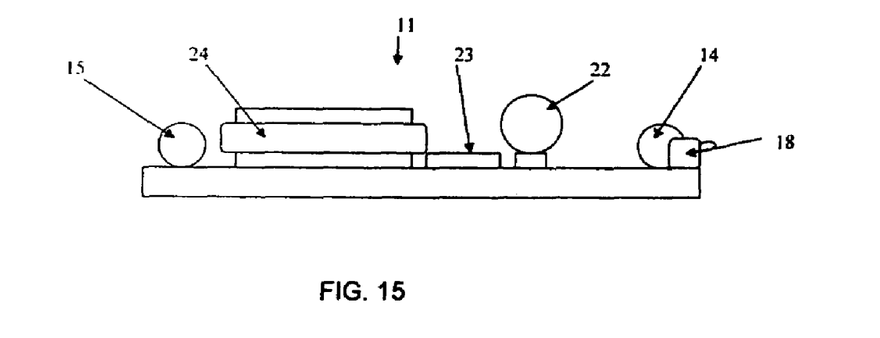
Figure 16:
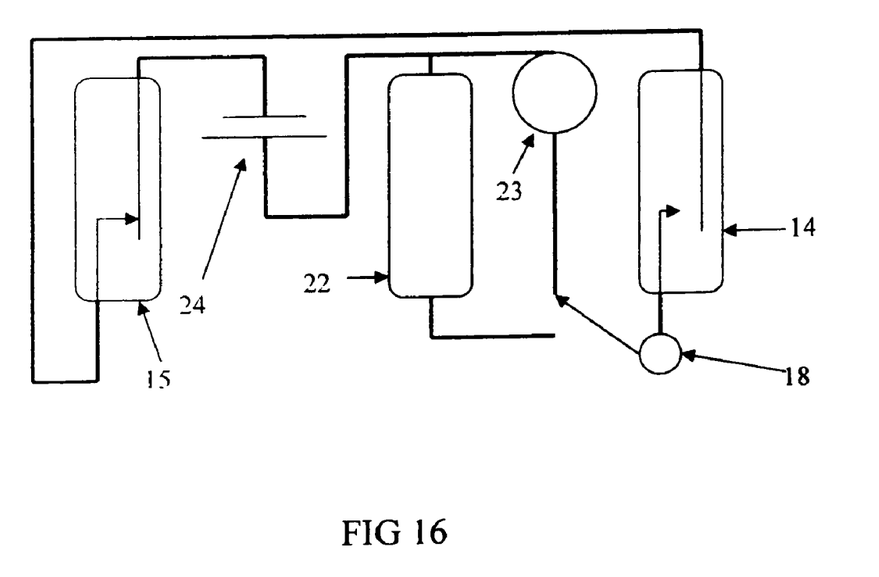

When pocket 19 that holds alarm module 11 is used to monitor the fluid level in an intravenous fluid bag, it is applied to a defined printed location 25 as generally illustrated and referenced in FIG. No. 11. It is contemplated that the printed location 25 may be printed or otherwise indicated at the time of manufacturing. An adhesive material on the outside back surface of pocket 19 allows it to be secured to the specified area on the front of the intravenous bag. In addition, a previously printed location 26 placed on the reverse side of the bag at the time of manufacture indicates the area to apply a 0.75 inch neodium disc magnet using the previously applied adhesive on one side of the magnet. Printed location 26 is generally illustrated and referenced in Figure No. When both pocket 19 and magnet (second magnetic field source 13) are in place and alarm module 11 (set to audible alarm) is positioned in pocket 19, the alarm will sound when the bag is near empty and the magnet (second magnetic field source 13) moves close to the sensor (second switch 14) in alarm module 11. Removing alarm module 11 from pocket 19 deactivates the alarm process.

Further, it is contemplated that the present invention comprises means for attaching fluid-dispensing/receiving receptacle 90 to a select receptacle support structure, the select receptacle support structure being selected from the group consisting of a user's body part (such as a leg 27 as illustrated and referenced in FIG. Nos. 1–5) and a user-assistive apparatus (such as an intravenous (IV) bag stand—not specifically illustrated). Typically, the user-assistive apparatus (such as an IV bag stand) is located adjacent a user. Notably, the dynamic fluid quantity, whether expelled urine or input saline solution, more properly maintains the user's biological functions.

Thus, the present invention contemplates a combination fluid receptacle 90 and alarm assembly 10, alarm assembly 10 for alerting a user of fluid receptacle 90 to a dynamic fluid quantity formed therein. Fluid receptacle 90 comprises a flexible fluid-impermeable casing, fluid passage means, and first and second receptacle surfaces 92 and 93. First and second receptacle surfaces 92 and 93 are adjustably distant from one another. The adjustably distant first and second receptacle surfaces 92 and 93 have a select alarm activation distance therebetween. Alarm assembly 10 comprises alarm module 11 and at least one magnetic field source. Alarm module comprises select user alert means, magnetically-actuated switch means, and power source means. Alarm module 11 is attached to first receptacle surface 92 and the magnetic field source (second magnetic field source 13) is attached to second receptacle surface 93. The fluid passage means enable dynamic fluid quantity development intermediate the first and second receptacle surfaces 92 and 93. The dynamic fluid quantity inherently has a dynamic volume, the dynamic volume for adjusting the linear distance intermediate first and second receptacle surfaces 92 and 93. The magnetic field source actuates the switch means when the select alarm activation distance is adjustably met. The actuated switch means electrically communicate the power source means with the select user alert means thus energizing the select user means. The energized select user alert means alert a user to the dynamic fluid quantity in the fluid receptacle.

The fluid passage means may be defined by fluid quantity adjustment means (e.g. fluid outlet 17), the fluid quantity adjustment means for adjusting the dynamic fluid quantity. The adjusted dynamic fluid quantity deactuates the switch means. The deactuated switch means interrupts electrical communication between the power source means and the select user alert means for resetting the select user alert means.

The present invention further contemplates an alarm assembly kit for outfitting a preexistent fluid receptacle. In this regard, as before, the alarm assembly kit is designed to alert a user of the fluid receptacle to a dynamic fluid quantity formed therein. The alarm assembly kit comprises an alarm module and at least one magnetic field source. The alarm module comprises select user alert means, magnetically-actuated switch means, and power source means. The alarm module is attachable to a first receptacle surface of a fluid receptacle. The magnetic field source is attachable to a second receptacle surface of the fluid receptacle. A dynamic fluid quantity is receivable intermediate the first and second receptacle surfaces, the dynamic fluid quantity having a dynamic volume, which functions to adjust the distance intermediate the first and second receptacle surfaces. The magnetic field source actuates the switch means when a select alarm activation distance is adjustably met. The actuated switch means electrically communicates the power source means with the select user alert means thus energizing the select user means. The energized select user alert means alert a user to the dynamic fluid quantity in the outfitted fluid receptacle. The kit may additionally comprise means for attaching the alarm module to the first receptacle surface and means for attaching the magnetic field source to the second receptacle surface. Further, the kit may include the fluid receptacle with our without preprinted indicia for attaching the alarm module and magnetic field sources to the corresponding receptacle surfaces.

While the above description contains much specificity, this specificity should not be construed as limitations on the scope of the invention, but rather as an exemplification of the invention. It is believed that the present invention thus teaches a fluid receptacle alarm assembly and/or kit, the fluid receptacle alarm assembly and/or kit comprising a fluid receptacle, an alarm module and at least one magnetic field source, depending on the type of application (two magnetic field sources for a fluid-receiving receptacle or application and one magnetic field source for a fluid-dispensing receptacle or application. The alarm module comprises select user alert means, magnetically-actuated switch means, and power source means. The alarm module is attachable to a first receptacle surface of the fluid receptacle and the magnetic field source is attachable to a second receptacle surface of the fluid receptacle. A dynamic fluid quantity is receivable intermediate the first and second receptacle surfaces, the dynamic fluid quantity having a dynamic volume for adjusting the distance intermediate the first and second receptacle surfaces. The magnetic field source actuates the switch means when a select alarm activation distance is adjustably met. The actuated switch means electrically communicates the power source means with the select user alert means. The energized select user alert means for alerting a user to the dynamic fluid quantity in the fluid receptacle. The first and second receptacle surfaces may each comprise structural locator indicia, the structural locator indicia enabling a user to locate first and second attachment locations. The first attachment location positions the attachable alarm module and the second attachment location positions the magnetic field source. The assembly or kit may further comprise means for attaching the alarm module to the first attachment location (such as pocket 19 or adhesive) and means for attaching the magnetic field source to the second attachment location (such as a pocket or adhesive).

Accordingly, although the invention has been described by reference to a preferred embodiment and at least one alternative embodiment, it is not intended that the novel assembly be limited thereby, but that modifications thereof are intended to be included as falling within the broad scope and spirit of the foregoing disclosure, the following claims and the appended drawings.

We claim:

1. An alarm assembly for alerting a user of a fluid-receiving receptacle to an incremental fluid quantity in the fluid-receiving receptacle, the fluid-receiving receptacle comprising a flexible fluid-impermeable casing, fluid passage means, and first and second receptacle surfaces, the first and second receptacles surfaces being adjustably distant from one another, the adjustably distant first and second receptacle surfaces having a select alarm activation distance therebetween, the alarm assembly comprising:

an alarm module and first and second magnetic field sources, the alarm module comprising select user alert means, magnetically-actuated first and second switches, and power source means, the alarm module and the first magnetic field source being attached to the first receptacle surface, the second magnetic field source being attached to the second receptacle surface, the first and second magnetic field sources actuating the first and second switches, the fluid passage means enabling a fluid quantity to increment intermediate the first and second receptacle surfaces, the incrementing fluid quantity having an incremental volume, the incremental volume increasing the distance intermediate the first and second receptacle surfaces, the second magnetic field source deactuating the second switch when the select alarm activation distance is adjustably met, the deactuated second switch electrically communicating the power source means with the select user alert means thus energizing the select user alert means, the energized select user alert means for alerting a user to the incremental fluid quantity in the fluid-receiving receptacle.

2. The alarm assembly of claim 1 wherein the fluid passage means comprise a fluid inlet and a fluid outlet, the fluid inlet for incrementing the incremental fluid quantity at an incremental rate, the fluid outlet for selectively decrementing the incremental fluid quantity at a decremental rate, the decremental rate being greater than the incremental rate thus selectively forming a decremental fluid quantity, the decremental fluid quantity for resetting the select user alert means.

3. The alarm assembly of claim 1 wherein the select user alert means is selected from the group consisting of audible alert means, visual alert means, and tactile alert means.

4. The alarm assembly of claim 1 wherein the first receptacle surface comprises a pocket, the pocket having open end for removably attaching the alarm module to the first receptacle surface.

5. The alarm assembly of claim 1 wherein the fluid-receiving receptacle is an inconspicuously worn urine-collection bag, the power source means are defined by a lithium battery, the first and second magnetically-actuated switches are defined by first and second dry reed switches, and the first and second magnetic field sources are defined by first and second neodium magnets, the lithium battery, the dry reed switches, and the neodium magnets each being minimally sized and shaped so as to maintain the inconspicuousness of the inconspicuously worn urine collection bag.

6. In combination, a fluid receptacle and an alarm assembly, the alarm assembly for alerting a user of the fluid receptacle to a dynamic fluid quantity formed therein, the fluid receptacle comprising a flexible fluid-impermeable casing, fluid passage means, and first and second receptacle surfaces, the first and second receptacle surfaces being adjustably distant from one another, the adjustably distant first and second receptacle surfaces having a select alarm activation distance therebetween, the alarm assembly comprising an alarm module and first and second magnetic field sources, the alarm module comprising select user alert means, magnetically-actuated switch means, and power source means, the alarm module and the first magnetic field source being attached to the first receptacle surface, the second magnetic field source being attached to the second receptacle surface, the fluid passage means enabling dynamic fluid quantity development intermediate the first and second receptacle surfaces, the dynamic fluid quantity having a dynamic volume, the dynamic volume for adjusting the distance intermediate the first and second receptacle surfaces, the first and second magnetic field sources cooperatively actuating the switch means when the select alarm activation distance is adjustably met, the actuated switch means electrically communicating the power source means with the select user alert means thus energizing the select user alert means, the energized select user alert means for alerting a user to the dynamic fluid quantity in the fluid receptacle.

7. The combination of claim 6 wherein the fluid receptacle is an inconspicuously worn fluid-collection bag, the power source means are defined by a lithium battery, the switch means are defined by at least one dry reed switch, and the first and second magnetic field sources are defined by first and second neodium magnets, the lithium battery, the dry reed switch, and the neodium magnets each being minimally sized and shaped so as to maintain the inconspicuousness of the inconspicuously worn fluid-collection bag.

8. A fluid receptacle alarm kit, the fluid receptacle kit comprising a fluid receptacle, an alarm module and first and second magnetic field sources, the alarm module comprising select user alert means, magnetically-actuated switch means, and power source means, the alarm module and the first magnetic field source being attachable to a first receptacle surface of the fluid receptacle, the second magnetic field source being attachable to a second receptacle surface of the fluid receptacle, a dynamic fluid quantity being receivable intermediate the first and second receptacle surfaces, the dynamic fluid quantity having a dynamic volume, the dynamic volume for adjusting the distance intermediate the first and second receptacle surfaces, the first and second magnetic field sources for cooperatively actuating the switch means when a select alarm activation distance is adjustably met, the actuateable switch means for electrically communicating the power source means with the select user alert means for energizing the select user means, the energizeable select user alert means for alerting a user to the dynamic fluid quantity in the outfitted fluid receptacle.

9. The kit of claim 8 wherein the first and second receptacle surfaces each comprise structural locator indicia, the structural locator indicia enabling a user to locate first and second attachment locations, the first attachment location for positioning the attachable alarm module and the first magnetic field source, and the second attachment location for positioning the second magnetic field source.

10. The kit of claim 9 comprising means for attaching the alarm module and the first magnetic field source to the first attachment location and means for attaching the second magnetic field source to the second attachment location.

* * * * *